United States Patent [19]
Chua et al.

[11] Patent Number: 5,626,131
[45] Date of Patent: May 6, 1997

[54] METHOD FOR INTERMITTENT GAS-INSUFFLATION

[75] Inventors: James Chua; Peter W. Salter, both of Tehachapi; Francis J. Kelly, Upland; Robert T. Wada, Claremont; Roy Y. Fujimoto, Upland, all of Calif.

[73] Assignee: Salter Labs, Arvin, Calif.

[21] Appl. No.: 480,354

[22] Filed: Jun. 7, 1995

[51] Int. Cl.$^6$ .................................................. A61M 16/00
[52] U.S. Cl. ........................ 128/204.23; 128/205.11; 128/205.24; 128/207.13; 128/207.18
[58] Field of Search .................... 128/204.18, 204.21, 128/204.23, 205.11, 205.22, 205.24, 207.13, 207.18

[56] References Cited

U.S. PATENT DOCUMENTS

| | | | |
|---|---|---|---|
| 3,972,327 | 8/1976 | Ernst et al. | 128/204.21 |
| 4,461,293 | 7/1984 | Chen | 128/204.23 |
| 4,462,398 | 7/1984 | Durkan et al. | 128/200.14 |
| 4,484,578 | 11/1984 | Durkan | 128/204.24 |
| 4,519,387 | 5/1985 | Durkan et al. | 128/204.23 |
| 4,570,631 | 2/1986 | Durkan | 128/204.23 |
| 4,584,996 | 4/1986 | Blum | 128/204.21 |
| 4,612,928 | 9/1986 | Tiep et al. | 128/204.23 |
| 4,681,099 | 7/1987 | Sato et al. | 128/204.23 |
| 4,686,974 | 8/1987 | Sato et al. | 128/204.23 |
| 4,686,975 | 8/1987 | Naimon et al. | 128/204.23 |
| 4,706,664 | 11/1987 | Snook et al. | 128/204.23 |
| 4,784,130 | 11/1988 | Kenyon et al. | 128/204.21 |
| 4,932,402 | 6/1990 | Snook et al. | 128/204.23 |
| 4,938,212 | 7/1990 | Snook et al. | 128/205.24 |
| 4,971,049 | 11/1990 | Rotariu et al. | 128/204.21 |

FOREIGN PATENT DOCUMENTS

84/01293  4/1984  WIPO.

OTHER PUBLICATIONS

Braun, Sheldon R., M.D., et al., "Comparison of Six Oxygen Delivery Systems for COPD Patients at Rest and During Exercise", Chest, vol. 102, No. 3, Sep. 1992, pp. 694–698.

Primary Examiner—Jennifer Bahr
Assistant Examiner—Eric P. Raciti
Attorney, Agent, or Firm—Shoemaker and Mattare, Ltd.

[57] ABSTRACT

An intermittent gas-insufflation apparatus insufflates a quantity of the gaseous fluid into an entrance of a respiratory system of a breathing patient during an exhalation interval of an immediate breathing cycle and into a subsequent inhalation interval of a successive breathing cycle. The intermittent gas-insufflation apparatus includes a valve assembly, a sensor and a controller. The valve assembly actuates between a closed state to prevent the gaseous fluid from flowing from a source of gaseous fluid to the patient and an opened state to establish gaseous fluid flow to the patient. The sensor detects changes in breathing pressure of the patient throughout the immediate breathing cycle and to generates sensor signals characteristic of the changes in the breathing pressure thereof. The controller receives and processes the sensor signals during either the inhalation interval of the immediate breathing cycle, the exhalation interval of the immediate breathing cycle or both and is responsive within the exhalation interval of the immediate breathing cycle to the sensor signals to actuate the valve assembly into the opened state so that the gaseous fluid flows from the source of gaseous fluid to the entrance into the respiratory system of the patient during the exhalation interval of the immediate breathing cycle and into the subsequent inhalation interval of the successive breathing cycle. Methods are also described for various exemplary embodiments of the present invention and for maintenance of blood-oxygen concentration for a patient receiving oxygen from a supplemental oxygen delivery system.

3 Claims, 7 Drawing Sheets

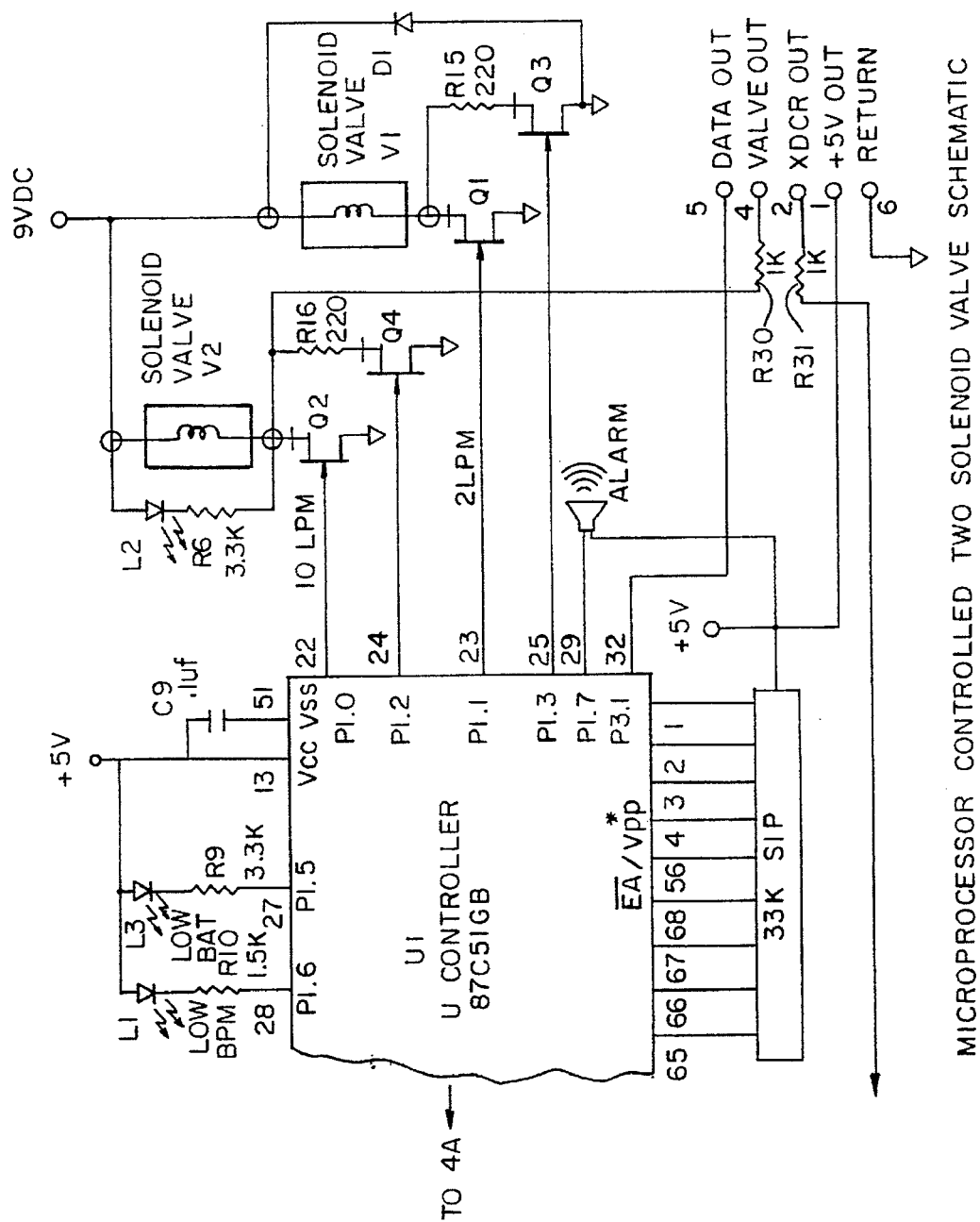

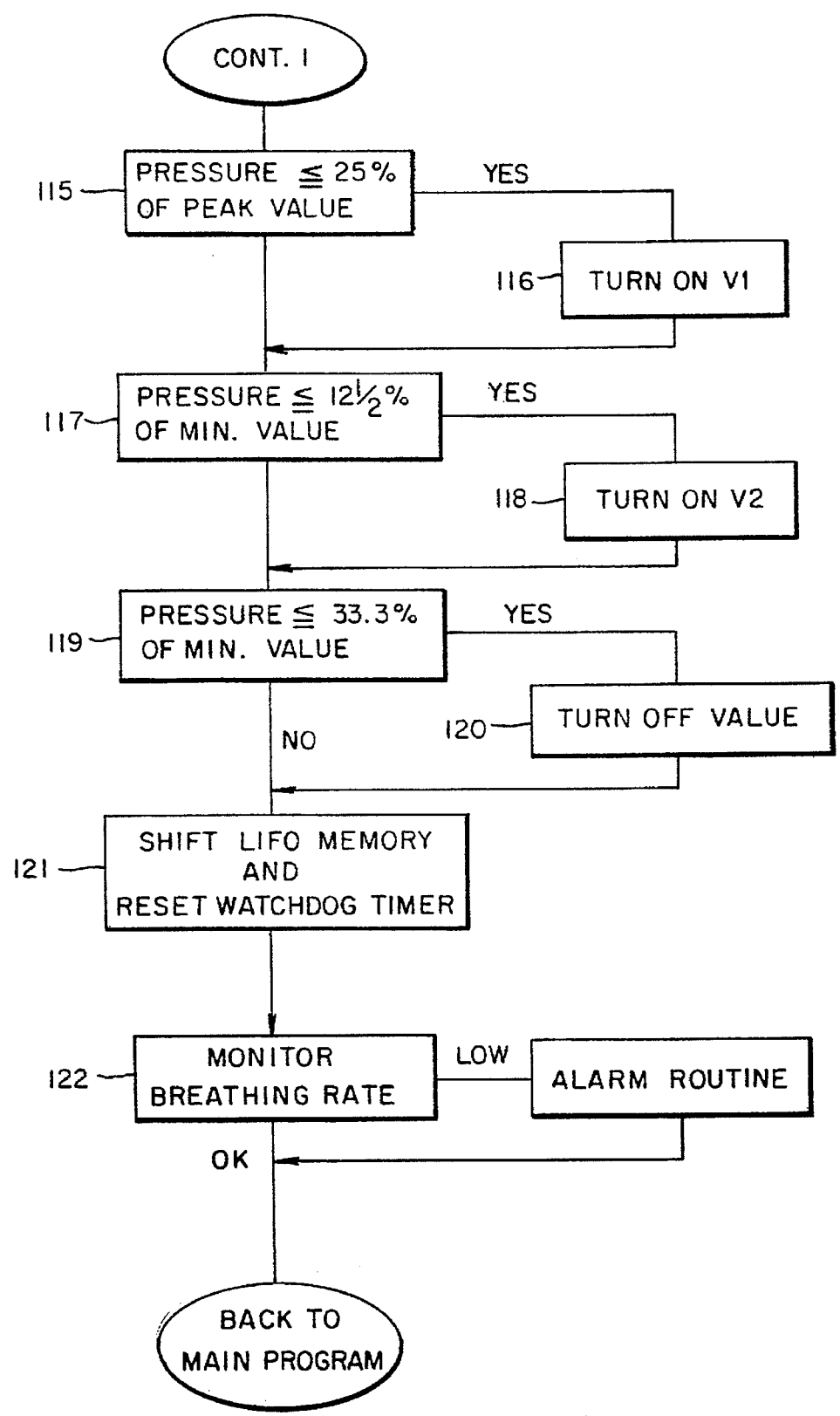

5,626,131

METHOD FOR INTERMITTENT GAS-INSUFFLATION

FIELD OF THE INVENTION

The present invention relates to an intermittent gas-insufflation apparatus and method for insufflating a quantity of a gaseous fluid into an entrance of a respiratory system of a breathing patient within each consecutive breathing cycle. More particularly, the present invention is directed to an intermittent gas-insufflation apparatus and method for determining during an inhalation interval and/or an exhalation interval of an immediate breathing cycle, the quantity of the gaseous fluid required by the patient under changing respiratory conditions and for insufflating the predetermined quantity of the gaseous fluid during the exhalation interval of the immediate breathing cycle and continuing into a subsequent inhalation interval of a successive breathing cycle. The present invention is particularly suitable in the medical industry for efficiently and cost effectively insufflating ambulatory patients having a need to supplement their breathing with oxygen in order to maintain sufficient levels of oxygen concentration in their blood under changing conditions of physical activity.

BACKGROUND OF THE INVENTION

Some patients suffer from deterioration of the lung function usually as a result of a chronic respiratory disease like bronchitis, emphysema and pulmonary fibrosis. When deterioration of the lung function occurs, the patient becomes hypoxemic. To treat hypoxemia and to relieve the ailments associated therewith, a health care provider will, most likely, prescribe supplemental oxygen to the patient so that the patient can inhale the supplemental oxygen along with ambient atmospheric air in order to maintain a sufficient oxygen concentration level in the blood stream.

Early supplemental oxygen delivery systems included a source of oxygen such as a tank of oxygen connected in fluid communication with a nasal cannula structure. Oxygen was delivered on a continuous flow basis, albeit a low, fixed flow rate, throughout the entire breathing cycle to the nose of the patient by a tube which interconnected the source of oxygen with the nasal cannula structure. Although efficacious in maintaining oxygen concentration levels in non-ambulatory patients, costly oxygen was lost to the ambient atmosphere since the continuous flow of oxygen was provided to the patient's nose during the entire breathing cycle, i.e., regardless if the patient was inhaling or exhaling. It was obvious that much of the oxygen that was being delivered to the nose of the patient was being wasted when using this continuous-flow supplemental oxygen delivery system. Furthermore, this early supplemental oxygen delivery system was unable to deliver variable quantities of oxygen in response to the changing oxygen demands of the patient when the patient's activity level changed. With the rising costs of medical care and the need to provide a more effective means of delivering oxygen to hypoxemic patients, other more effective oxygen delivery systems were developed.

To better comprehend the deficiencies of these prior art supplemental oxygen delivery systems and devices that conserved oxygen during operation, it would be beneficial to understand the breathing cycle of the patient before discussion of this prior art. When plotting the breathing pressure of the patient as a function of time, one breathing cycle generally appears as a modified sine wave. The positive breathing pressure of the sine wave as it rises then falls relative to ambient air pressure reflects the exhalation interval of the breathing cycle; correspondingly, the negative breathing pressure of the sine wave as it continues to fall after termination of the exhalation cycle then rises relative to the ambient air pressure reflects the inhalation interval of the breathing cycle. However, in reality, the sine wave of the breathing cycle is skewed whereby the exhalation interval of the skewed sine wave constitutes on an average of about two thirds of the breathing cycle while the inhalation interval of the skewed sine wave constitutes on an average of one third of the breathing cycle.

Furthermore, the respiratory system of the patient includes the passageway to the lungs comprising the nares of the nose, the nasal cavity and the trachea which together provide a conduit for transporting ambient atmospheric air to a person's lungs. This passageway is anatomically dead space that, after the exhalation interval, is now filled with exhaled air which, in turn, becomes the first quantity of inhaled air during the subsequent inhalation interval. By way of example only, on the average, this anatomically dead space retains about the first one third ($\frac{1}{3}$rd) of the quantity of air for the next inhalation. The remaining two thirds ($\frac{2}{3}$) of the quantity of air required for breathing is provided by fresh ambient atmospheric air during the subsequent inhalation interval. Only one half ($\frac{1}{2}$) of this fresh ambient air reaches the lungs for gaseous exchange, i.e., the second one third ($\frac{1}{3}$) of the required air (or the first one half ($\frac{1}{2}$) of the fresh air) is carried to the lungs and the last one third ($\frac{1}{3}$rd) of the required air (or the second one half ($\frac{1}{2}$) of the fresh air) remains in the anatomically dead space. Therefore, on the average, only 16% to 17% of the breathing cycle brings fresh air or fresh air combined wit insufflation gas to the lungs and this occurs only during the first one half ($\frac{1}{2}$) of the inhalation interval of the breathing cycle.

In response to the waste of oxygen associated with the early prior art supplemental oxygen delivery systems that provided a continuous flow of oxygen throughout the entire breathing cycle, many other prior art systems and devices have been developed and implemented for delivery of supplemental oxygen to patients which included oxygen-conserving features. Some of these devices were characterized as being capable of providing oxygen "on demand" to the patient or "on the go". Generally, "on demand" meant in these systems that oxygen was not delivered to the patient until after the beginning of the inhalation interval of the breathing cycle and that no oxygen was delivered to the patient during any portion of the exhalation interval of the breathing cycle. Since oxygen was not delivered to the patient during the exhalation interval which constitutes two thirds of the entire breathing cycle, significant quantities of oxygen were conserved. Two types of the "on demand" supplemental oxygen delivery systems are discussed immediately below.

U.S. Pat. No. 4,462,398 and U.S. Pat. No. 4,519,387 to Durkan et al. reveal respirating gas supply methods and apparatuses designed to conserve the respirating gas during patient insufflation. A control circuit responsive to a sensor operates a valve to supply pulses of respirating gas through a single hose cannula to a respiratory system of a patient when negative pressure indicative of the initial stage of inspiration is sensed by the sensor. The pulse of gas delivered to the respiratory system can have a preselected pulse profile. This method provides for supplying a fixed volume of supplemental respiratory gas per unit of time. The volumetric flow rate of the supplemental respiratory gas is preset and the time duration of each application of the supplemental respiratory gas is preselected, thereby providing a fixed volume of respiratory gas after the beginning of inhalation.

Also, this method provides for a minimal delay interval between successive applications of respiratory gas and such delay interval is also predetermined since the time interval for respiratory gas flow is preset for a time less than the time of the inspiration.

Another prior art supplemental oxygen delivery system designed to conserve respiratory gas by delivering oxygen "on demand" only during inhalation is described in U.S. Pat. No. 4,612,928 to Tiep et al. which discloses both a method and apparatus for supplying a gas to a body. The apparatus and method are employed to minimize the amount of oxygen needed to maintain a specific oxygen concentration level in the blood of an individual. The apparatus includes a transducer and other circuit components to obtain a first series of pulses or signals corresponding to the individual's breath rate. A divider or counter processes the signals or pulses of the first series to create a second series of pulses or signals corresponding to periodic pulses or signals of the first series. The pulses or signals of the second series are used to periodically open a valve to deliver oxygen to the individual at about the start of the inhalation interval of the individual's periodic breathing cycles.

In U.S. Pat. No. 4,457,303 and U.S. Pat. No. 4,484,578, Durkan recognizes that oxygen delivered at the end of the inhalation interval of the breathing cycle is wasteful. These two patents describe respirator apparatuses and methods therefor. In brief, a fluidically-operated respirator comprises an apneic event circuit and a demand gas circuit. The apneic event circuit comprises a variable capacitance device and an exhaust means which rapidly discharges fluid from the circuit when inhalation occurs. The demand gas circuit of the respirator supplies respirating gas to a patient at the beginning of inhalation and for a time period which is a fraction of the duration of the inhalation. Thus, these patents also follow the reasoning that insufflation at the beginning of inhalation will effectively supply the respirating gas to the patient.

One prior art supplemental oxygen delivery system begins to deliver a steady flow of oxygen during a later stage of the exhalation interval and through an advanced stage of the inhalation interval of the breathing cycle and superimposes upon this steady flow of oxygen a peak pulse flow of oxygen at the beginning of inhalation. This is described in U.S. Pat. No. 4,686,974 to Sato et al. which discloses a breath-synchronized gas-insufflation device. This device includes a gas source, a valve, an insufflating device, a sensor, and an operational controller. The valve is connected to the gas source so as to regulate flow rate and duration of the gas flow from the gas source. The insufflating device is connected to the valve so as to insufflate the gas therefrom toward a respiratory system of a living body. The sensor is exposed to respiration of the living body and produces electric signals which must distinctively indicate an inhalation interval and an exhalation interval of the breathing cycle. The operational controller receives the electric signals from the sensor and produces control signals to the valve so that gas insufflation starts before the beginning of the inhalation interval and ends before termination of the inhalation interval while providing a short pulse-like peak flow of a large amount of the gas in an early stage of the inspiratory interval. Specifically, steady insufflation of the gas starts before the beginning of each inhalation and the pulse-like peak flow insufflation of the gas is superimposed on the steady insufflation for a short period of time after the beginning of the inhalation. An arbitrary time interval based upon an average exhalation period and an average inhalation period is chosen to trigger and end insufflation during the breathing cycle.

Although the prior art devices discussed hereinabove indeed conserved oxygen, they failed to address the problem related to the changing respiratory needs of the patient that vary with different patient activity levels. When a patient requiring supplemental oxygen is at rest, relatively small quantities of oxygen are needed to maintain appropriate levels of oxygen concentration in the blood and thereby prevent what is termed "desaturation". With an increase in the physical activity of a patient, larger quantities of oxygen are needed to maintain appropriate levels of oxygen concentration in the blood compared to when the patient is at rest.

In U.S. Pat. No. 4,706,664, Snook et al. disclose a pulse-flow supplemental oxygen apparatus which yields savings in oxygen while affording the patient the physiological equivalent of a prescribed continuous stream of oxygen. The apparatus includes a demand oxygen valve operated in a pulse mode by means of electronic control circuitry. Through an appropriate sensor, the electronic control circuitry monitors the patient's breathing efforts and gives a variable timed pulse of oxygen to increase the volume delivered to the patient during the very initial stage of each inhalation interval of the breathing cycle or breaths. Pulse volume variability is based upon a measured parameter characterizing a plurality of the patient's preceding breathing cycles. The elapsed time interval of the patient's three preceding breathing cycles is measured to effectively measure the rate of the breathing cycles. These breath-characterizing parameters, together with data characterizing the prescribed continuous oxygen flow to be matched, enable the apparatus to give the desired dose-variability.

U.S. Pat. No. 4,584,996 to Blum reveals a method and apparatus for intermittent administration of supplemental oxygen to patients with chronic lung disfunction. The apparatus is programmable for administering the specific oxygen requirements of the patient and is responsive to changes in these oxygen requirements with increased patient activity. The patient's arterial blood oxygen level is measured while supplying oxygen to the patient during inspiration to determine the number of breathing cycles required to reach a first higher arterial blood oxygen level and is again measured without supplemental oxygen to determine the number of breathing cycles required to diminish the arterial blood oxygen level to a second, lower level. These two cycle numbers are utilized in an algorithm which is applied as a program to the apparatus having a breathing cycle sensor, a counter and control valve. The control valve provides a regulated flow of supplemental oxygen to a nasal cannula for a predetermined number of "ON" breathing cycles and to shut off the flow for a preset number of "OFF" breathing cycles sequentially and repetitively, thereby conserving oxygen while medically monitoring the patient's blood oxygen levels. The oxygen conservation features of this apparatus are further enhanced by turning off the oxygen flow during the exhalation interval of each breathing cycle throughout the "ON" breathing cycles. As the respiratory rate of the patient increases with patient activity, the duration of the "ON" and "OFF" periods changes accordingly.

In U.S. Pat. No. 4,686,975, Naimon et al. teaches a supplemental respiratory device that uses electronic components to intermittently regulate the flow of a respirable gas to a user on a demand basis. By monitoring small changes in the relative airway pressure, this respiratory device supplies gas only when an inhalation is detected. This respiratory device can also vary the duration of the gas delivery time to compensate for changes in the user's breath rate, thereby attempting to adjust for changes in the patient's respiratory needs based upon activity.

Presently, many manufacturers are marketing oxygen conserver devices which are adapted to retrofit onto typical supplemental oxygen delivery systems that employ any type of oxygen source such as portable oxygen tanks, oxygen concentrators or wall outlet supplies often utilized in hospitals. These oxygen conserver devices are adapted to be interposed between the oxygen source and a conventional nasal cannula structure. Medisonic U.S.A., Inc. of Clarence, N.Y., manufactures an oxygen conserver device entitled MEDISO$_2$NIC Conserver. It conserves oxygen by interrupting the flow of oxygen from the source to the patient during the exhalation interval of the patient's breathing cycle. Chad Therapeutics, Inc. of Chatsworth, Calif., manufacturers an oxygen conserver device bearing a registered trademark, OXYMATIC® Electronic Oxygen Conserver. Chad's oxygen conserver eliminates oxygen waste during both the exhalation interval and the later portion of the inhalation interval of the breathing cycle. TriTec, Inc. of Columbia, Md., manufactured a demand oxygen cannula for portable oxygen systems that also responded to the negative pressure of inhalation. Smith-Perry Corporation of Surrey, British Columbia, Canada, manufactures The VIC (Voyager Intermittent Controller) Breathsaver that senses every breath of the patient and delivers a measured dose of oxygen only when the patient inhales. Pulsair, Inc. of Fort Pierce, Fla., manufactures an oxygen management system that delivers oxygen to the patient "on demand" at the initiation of inhalation. The Henry G. Dietz Co., Inc. of Long Island City, N.Y., manufactures an oxygen conserver device entitled HALA'TUS 1 which conserves oxygen by sensing when inhalation takes places and delivers the oxygen only during inhalation.

None of these oxygen conserver devices deliver oxygen to the patient during any stage of exhalation.

Although many improvements have been made to conserve oxygen while employing supplemental oxygen delivery systems, there remains a need in the industry to more efficiently and effectively deliver sufficient concentrations of oxygen to a patient under changing conditions of physical activity while simultaneously conserving oxygen. There is a need to provide an intermittent gas-insufflation apparatus that can supply the appropriate quantity of oxygen to be delivered to the patient during an exhalation interval of an immediate breathing cycle and into a subsequent inhalation interval of a successive breathing cycle. It would be advantageous if delivery of the appropriate quantity and concentration of oxygen commences during the exhalation interval of the immediate breathing cycle. It would also be advantageous if this intermittent gas-insufflation apparatus could deliver the appropriate quantity and concentration of oxygen during the exhalation interval of the immediate breathing cycle and into the subsequent inhalation interval of the successive breathing cycle. There is also a need for an intermittent gas-insufflation apparatus that can determine an appropriate flow rate profile during the immediate breathing cycle. This flow rate profile would be designed to deliver the appropriate quantity and concentration of oxygen to the patient commencing during the exhalation interval of the immediate breathing cycle and into the subsequent breathing cycle. It would be advantageous if the intermittent gas-insufflation apparatus delivers a portion of the appropriate quantity of oxygen at a nominal flow rate to the patient during the exhalation interval of the immediate breathing cycle so that a portion of the residual air found in the nasal cavity from a prior breathing cycle can be purged therefrom and a remaining portion of this residual air becomes enriched with oxygen in preparation for the subsequent inhalation interval of the successive breathing cycle. Also, there is a need for an intermittent gas-insufflation apparatus that terminates oxygen insufflation during the subsequent inhalation interval of the successive breathing cycle. It would be advantageous if the intermittent gas-insufflation apparatus would cease to deliver the appropriate quantity of oxygen during the subsequent inhalation interval of the successive breathing cycle before a negative peak pressure value determined in the immediate breathing cycle is reached in the successive breathing cycle. The present invention satisfies these needs and provides these advantages.

OBJECTS AND SUMMARY OF THE INVENTION

It is an object of the present invention to provide a new and useful intermittent gas-insufflation apparatus that determines the appropriate quantity of oxygen to be delivered to the patient during an immediate breathing cycle.

It is another object of the present invention to provide an intermittent gas-insufflation apparatus so that the appropriate quantity of oxygen is delivered during an exhalation interval of the immediate breathing cycle and into a subsequent inhalation interval of a successive breathing cycle.

It is yet another object of the invention is to provide an intermittent gas-insufflation apparatus that can determine an appropriate flow rate profile during the immediate breathing cycle.

A still further object of the present invention is to provide an intermittent gas-insufflation apparatus that delivers the appropriate quantity of oxygen at the appropriate flow rate profile during the exhalation interval of the immediate breathing cycle and into the subsequent inhalation interval of the successive breathing cycle.

Yet another object of the present invention is to provide an intermittent gas-insufflation apparatus that delivers a portion of the appropriate quantity of oxygen at a maximum flow rate to the patient at approximately a beginning stage of the subsequent inhalation interval of the successive breathing cycle.

Yet still another object of the present invention is to provide an intermittent gas-insufflation apparatus which commences to deliver the appropriate quantity of oxygen during the exhalation of the immediate breathing cycle so that a portion of the residual air found in the nasal cavity from a prior breathing cycle is purged therefrom and a remaining portion of this residual air becomes enriched with oxygen in preparation for the forthcoming subsequent inhalation interval.

A still further object of the present invention is to provide an intermittent gas-insufflation apparatus that terminates oxygen insufflation during the subsequent inhalation interval of the successive breathing cycle and, preferably before a negative peak pressure value generated in the immediate breathing cycle is reached in the successive breathing cycle.

As a result of the above observations with respect to prior art devices, it was a primary object of the hereindescribed invention to improve the oxygenation process provided by previous inventions and at the same time increase efficiency of oxygen use, provided that increase in efficiency is not at the expense of attaining required oxygen levels. To accomplish these objectives, the patient is fitted with a nasal cannula equipped with both sense and gas delivery capability. Insufflating gas is supplied from a gas source to the patient through the gas delivery capability of the nasal cannulae. In the present invention, the gas delivery is controlled in a manner to deliver a preselected flow rate beginning before the end of the patient's exhalation and then increased to a higher predetermined flow rate at a preselected segment of the inhalation interval of the patient's breathing cycle preferably during the first one third of the patient's inhalation cycle before the peak of inhalation flow is achieved by the patient's inhalation effort. The predetermined flow rate of insufflation gas delivered during inhalation can be a fixed flow rate or a variable flow rate where both deliver a predetermined volume of insufflation gas before the peak of inhalation in order to maintain a desired blood oxygen concentration consistent with the physiological need of the patient, either required by the patient's physical activity or diagnosed condition.

The apparatus and method for achieving the desired insufflation gas delivery to obtain the amount of insufflation gas at the appropriate portions of the patient's breathing cycle will be described in more detail hereinafter.

BRIEF DESCRIPTION OF THE DRAWINGS

FIGS. 5A and 5B are a flow chart of the software program which operates the controller of the intermittent gas-insufflation apparatus of the present invention.

DETAILED DESCRIPTION OF THE EXEMPLARY EMBODIMENTS

Figure 1:
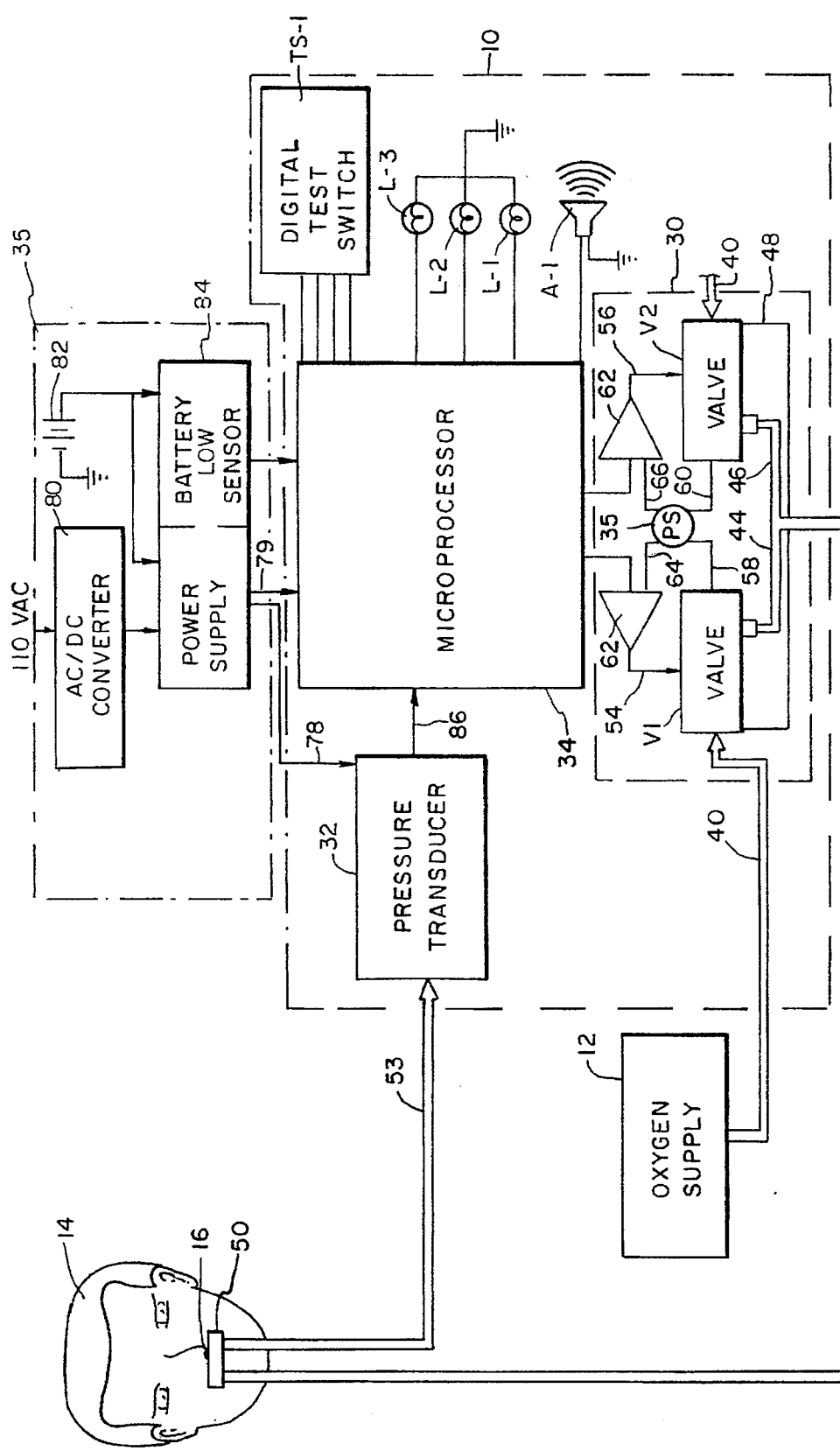
FIG. 1 is a schematic diagram of a first exemplary embodiment of an intermittent gas-insufflation apparatus of the present invention shown operably connected to and between a breathing patient and a source of pressurized gaseous fluid.

An intermittent gas-insufflation apparatus of the present invention is adapted to be disposed between and in fluid communication with a source of pressurized gaseous fluid such as oxygen and a breathing patient. The intermittent gas-insufflation apparatus is operative to insufflate a quantity of the gaseous fluid, i.e., oxygen, into an entrance of a respiratory system of the patient after an inhalation interval and during an exhalation interval of an immediate breathing cycle and into a subsequent inhalation interval of a successive breathing cycle of the patient. For purposes of explaining the intermittent gas-insufflation apparatus of the present invention, it would be beneficial to discuss several terms used throughout the description of the exemplary embodiments of the present invention to better understand the operation and components thereof. Quotation marks are employed to highlight the first usage of each term in the explanation discussed below.

A "breathing cycle" occurs when the patient first inhales and then exhales; the breathing cycle commences when the patient begins to inhale and terminates when the patient completes exhalation. As a result, a breathing cycle consists of an "inhalation interval" and an "exhalation interval" which follows the inhalation interval. A convention used for explanation purposes only of the exemplary embodiments of the present invention is that the inhalation interval is sensed by detection of "negative pressure values" relative to an ambient pressure environment which are generated as the patient inhales and the exhalation interval is sensed by detection of "positive pressure values" relative to the ambient pressure environment which are generated as the patient exhales. Particularly useful for explanation of the first exemplary embodiment of the intermittent gas-insufflation apparatus of the present invention is a "negative peak pressure value" which occurs as the lowest pressure value detected during the inhalation interval of the immediate breathing cycle and a "positive peak pressure value" which occurs as the highest pressure value detected during the exhalation interval of the immediate breathing cycle. These negative and positive peak pressure values are employed for the operation of the first exemplary embodiment of the intermittent gas-insufflation apparatus of the present invention. Furthermore, "immediate breathing cycle" and "successive breathing cycle" are used herein as a convention only to explain the operation of the present invention. As suggested by the terms themselves, the immediate breathing cycle is the breathing cycle in which the patient is currently breathing and the successive breathing cycle follows the immediate breathing cycle. In reality, once the "immediate breathing cycle" terminates, the "successive breathing cycle" now becomes the immediate one and the terminated immediate one becomes a preceding breath cycle. It would be understood by one of ordinary skilled in the art that a patient breaths only during the immediate breathing cycle. Additionally, "changes in breathing pressure" can be construed as either actual changes of breathing pressure or changes in the rate of breathing pressure.

Figure 2:
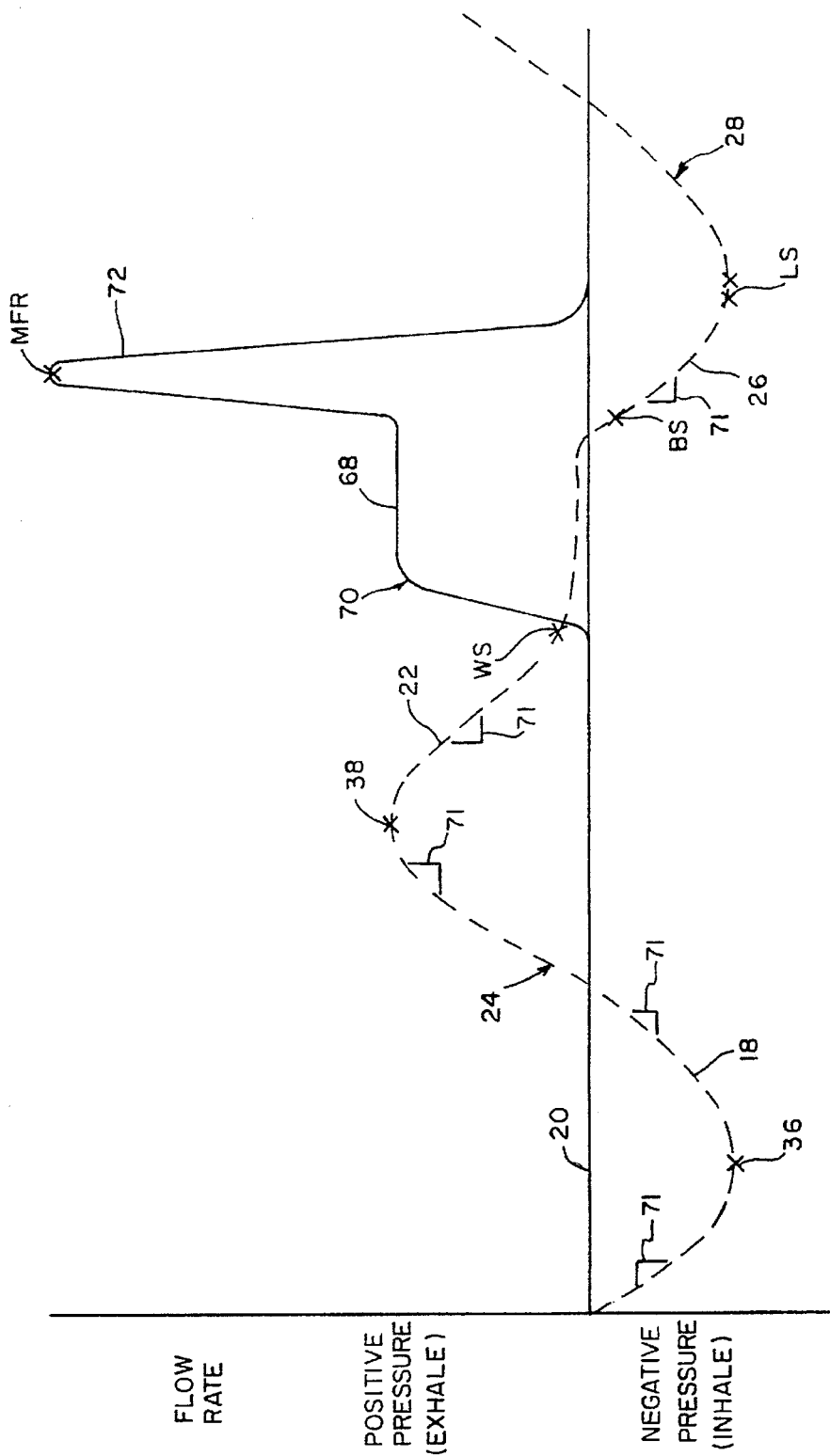
FIG. 2 is a graph illustrating a flow rate profile of the gaseous fluid being delivered to the patient superimposed over an inhalation interval and an exhalation interval of an immediate breathing cycle and a subsequent inhalation interval of a successive breathing cycle.

A first exemplary embodiment of an intermittent gas-insufflation apparatus 10 of the present invention is generally introduced in FIGS. 1 and 2. Intermittent gas-insufflation apparatus 10 is adapted to be disposed between and in fluid communication with a source 12 of pressurized gaseous fluid and a breathing patient 14. It is preferred that the gaseous fluid is oxygen although the gaseous fluid could also be selected from a group consisting of air, nitrous oxide, ether and other gases normally administered to human beings and animals. Intermittent gas-insufflation apparatus 10 is operative to insufflate a quantity of the gaseous fluid into an entrance 16 of a respiratory system of patient 14. Typically, entrance 16 is a nose or mouth of patient 14, although, in some instances, entrance 16 could be both the nose and the mouth of patient 14. With reference to FIG. 2, the quantity of the gaseous fluid (solid line) is continuously insufflated after an inhalation interval 18 (dotted line below base line 20) and during an exhalation interval 22 (dotted line above base line 20) of an immediate breathing cycle 24. As stated above, immediate breathing cycle 24 is inhalation interval 18 plus exhalation interval 22. Insufflation of the gaseous fluid continues into a subsequent inhalation interval 26 of a successive breathing cycle 28 of patient 14.

Again, with reference to FIG. 1, intermittent gas-insufflation apparatus 10 includes a valve assembly 30, a sensor 32, a controller 34 and a power source 35 which is operative to energize valve assembly 30, sensor 32 and controller 34. Valve assembly 30 is disposed between and in fluid communication with source 12 of gaseous fluid and entrance 16 into the respiratory system of patient 14. Valve assembly 30 is operative to actuate between a closed state and an opened state. In the closed state, fluid communication is interrupted so that the gaseous fluid is prevented from flowing from source 12 of gaseous fluid to entrance 16 into the respiratory system of patient 14. In the opened state, fluid communication is established so that the gaseous fluid flows from source 12 of gaseous fluid to entrance 16 into the respiratory system of patient 14.

Sensor 32 in a form of a pressure transducer is in fluid communication with entrance 16 of the respiratory system of patient 14 and is operative to detect changes in breathing pressure (represented by the dashed sinusoid line in FIG. 2) of breathing patient 14 relative to an ambient pressure environment as patient 14 breaths. Although not by way of limitation, it is preferred, for the first exemplary embodiment of the present invention, that the detected changes in breathing pressure are actual changes in the breathing pressure. Specifically, sensor 32 is operative to detect changes in breathing pressure throughout inhalation and exhalation intervals 18 and 22 respectively of immediate breathing cycle 24 of patient 14. Sensor 32 is further operative to generate sensor signals characteristic of the changes in breathing pressure of immediate breathing cycle 24. These changes in breathing pressure plotted as a function of time (base line 20) is represented by the dashed sinusoidal line shown in FIG. 2.

Controller 34 in a form of a microprocessor is coupled to and between sensor 32 and valve assembly 30 (FIG. 1) and is operative to receive and process the sensor signals to determine a negative peak pressure value 36 (FIG. 2) which occurs during inhalation interval 18 of immediate breathing cycle 24 and a positive peak pressure value 38 which occurs during exhalation interval 22 of immediate breathing cycle 24. Controller 34 is responsive within exhalation interval 22 of immediate breathing cycle 24 when a first predetermined percentage of positive peak pressure value 38 is achieved which is discussed in more detail below. Upon achieving the first predetermined percentage of positive peak pressure value 38, valve assembly 30 is actuated into the opened state so that the gaseous fluid flows from source 12 of gaseous fluid to entrance 16 into the respiratory system of patient 14 during exhalation interval 22 of immediate breathing cycle 24 and into inhalation interval 18 of successive breathing cycle 28. Controller 34 is further responsive within subsequent inhalation interval 26 of successive breathing cycle 28 when a second predetermined percentage of negative peak pressure value 36 is achieved to actuate valve assembly 30 into the closed state so that the gaseous fluid is prevented from flowing from source 12 of gaseous fluid to entrance 16 into the respiratory system of patient 14.

Controller 34 is further responsive within subsequent inhalation interval 26 of successive breathing cycle 28 when a third predetermined percentage of negative peak pressure value 36 is achieved to further actuate valve assembly 30 into an enhanced opened state. In the enhanced opened state, an additional quantity of gaseous fluid flows from source 12 of gaseous fluid to entrance 16 into the respiratory system of patient 14 after exhalation interval 22 of immediate breathing cycle 24 and before a remaining portion of subsequent inhalation interval 26 of successive breathing cycle 28. Alternatively, valve assembly 30 could be actuated into the enhanced opened state during exhalation interval 22 of immediate breathing cycle 24, if desired.

The first, second and third predetermined percentages are determined clinically by a clinician for each individual patient. Preferably, at least the first and second predetermined percentages are tailored to respiratory needs of each individual patient although the third predetermined percentage can be tailored to respiratory needs of each individual patient. Thus, the intermittent gas-insufflation apparatus of the present invention is tailored to the patient's particular supplementary oxygen needs. Factors which might be considered by the clinician are weight, height, physical condition, severity of lung dysfunction and the like. The first and second predetermined percentages are selected from a range of 10% to 80%. The first and second predetermined percentages are different from one another or they could be the same. The first and second predetermined percentages are selected from a range of 10% and 80% inclusive. Preferably, the first predetermined percentage is 25%; the second predetermined percentage is 33.3%.The third predetermined percentage is selected from a range of 1% and 25%inclusive as long as it is less than the second predetermined percentage. Preferably, the third predetermined percentage is 12.5%.

For the first exemplary embodiment of intermittent gas-insufflation apparatus 10 of the present invention, valve assembly 30 includes a first solenoid valve V1 and a second solenoid valve V2. First solenoid valve V1 is operative between a first closed state and a first opened state; second solenoid valve V2 is operative between a second closed state and a second opened state. Each of first and second solenoid valves V1 and V2 is independently connected in fluid communication to and between source 12 of pressurized gas and entrance 16 into the respiratory system of patient 14. Gas supply tubing 40 connects first and second solenoid valves V1 and V2 to source 12 of pressurized gaseous fluid. Respective ones of valve tubings 44 and 46 connect first and second solenoid valves V1 and V2 to a manifold 48. Manifold 48, in turn, is connected to a nasal cannula 50 via a single gas delivery tube 52. First and second solenoid valves V1 and V2 are independently connected electrically to controller 34 via line 54 and 56 and to power source 35 via lines 58 and 60. First and second solenoid valves V1 and V2 have a valve driver 62 interposed in respective lines 54 and 56 and each valve driver 62 is electrically connected to power source 35 via respective lines 64 and 66. Each valve driver 62 is electrically connected to controller 34 via lines 67 and 69.

Nasal cannula 50, gas delivery tube 52 and a sensing tube 53 are components of a conventional cannula structure commonly known in the art. In brief, nasal cannula 50 is sized and adopted to be received by and secured proximate to the entrance of the respiratory system of breathing patient 14. Nasal cannula 50 has a septum (not shown) dividing nasal cannula 50 into a gas delivery conduit and a sensing conduit which are isolated from fluid communication with one another. The gas delivery conduit is in fluid communication with valve assembly 30 via gas delivery tube 52 and the sensing conduit is in fluid communication with sensor 32 via sensing tube 53. Thus, nasal cannula 50, sometimes referred to as a split cannula, can both detect changes in breathing pressure and deliver oxygen to the patient simultaneously.

Again, with reference to FIG. 2, first solenoid valve V1 is operative to actuate from the first closed state to the first opened state during exhalation interval 22 of immediate breathing cycle 24 and from the first opened state to the first closed state at a later stage "LS" of subsequent inhalation interval 26 of successive breathing cycle 28. Thus, the gaseous fluid flows (solid line) as shown during exhalation interval 22 of immediate breathing cycle 24 which begins at a waning stage "WS" of exhalation interval of the immediate breathing cycle. Waning stage "WS" represents the first predetermined percentage multiplied by positive peak pressure value 38. When in the first opened state, the gaseous fluid flow builds to a steady state flow as shown by a flat solid line portion 68 of flow trace 70. Meanwhile, second solenoid valve V2 is operative to actuate from the second closed state to the second opened state at approximately a beginning stage "BS" of subsequent inhalation interval 26 of successive breathing cycle 28 thereby causing the enhanced opened state of valve assembly 30. Beginning stage "BS" represents the third predetermined percentage multiplied by the peak negative pressure value of the immediate breathing cycle which is used in the subsequent inhalation interval. In the second opened state of second solenoid valve V2, the additional gaseous fluid flows as a high flow-rate pulse reflected by the spiked solid line portion 72 of flow trace 70. The second solenoid valve V2 is operative to actuate and from the second opened state to the second closed state at later stage "LS" of subsequent inhalation interval 26 of successive breathing cycle 28. Later stage "LS" represents the second predetermined percentage multiplied by the negative peak pressure value of the immediate breathing cycle. Thus, although not by way of limitation, first solenoid valve V1 and second solenoid valve V2 actuate to their respective closed states simultaneously. Preferably, later stage "LS" occurs before the negative peak pressure value of the subsequent inhalation interval. Furthermore, first solenoid valve V1 and second solenoid valve V2 respectively actuate to the first closed state and the second closed state when the second predetermined percentage of negative peak pressure value 36 is achieved. In any event, gaseous fluid flows at a flow rate selected from a flow rate range of 0.5 liters per minute and 12 liters per minute inclusive.

One of ordinary skill in the art would appreciate that the intermittent gas-insufflation apparatus of the present invention operates within its own operating cycle which is hereinafter deemed an "insufflation operating cycle". The insufflation operating cycle begins at the negative peak pressure value of the inhalation interval of the immediate breathing cycle, continues through the exhalation interval of the immediate breathing cycle and terminates before the negative peak pressure value of a subsequent inhalation interval of the successive breathing cycle. A skilled artisan would understand that the insufflation operating cycle of the present invention is considered to be phase shifted forward by 90 degrees relative to the patient's normal breathing cycle. Additionally, one of ordinary skill in the art would appreciate that the present invention generates these negative and positive peak pressure values to activate the present invention during the immediate breathing cycle and utilizes reference pressures from the immediate breathing cycle to de-activate the present invention in the successive breathing cycle. Moreover, it is appreciated that the intermittent gas insufflation apparatus of the present invention detects changes in pressure, utilizes these detected changes for delivery of the gaseous fluid, and then commences delivery of the gaseous fluid to the patient within the patient's immediate breathing cycle, which has not heretofore been accomplished by any of the prior art gas insufflation devices.

It follows from the first exemplary embodiment of intermittent gas-insufflation apparatus 10 of the present invention, a method can be employed for intermittently insufflating a gaseous fluid from a pressurized gaseous fluid source 12 into entrance 16 of a respiratory system of a breathing patient 14 after inhalation interval 18 and during exhalation interval 22 of immediate breathing cycle 24 and into subsequent inhalation interval 26 of successive breathing cycle 28. The first step of this method is determining the negative peak pressure value which occurs during inhalation interval 18 of immediate breathing cycle 24. The next step is determining the positive peak pressure value which occurs during exhalation interval 22 of immediate breathing cycle 24. The next step includes commencing delivery of the gaseous fluid to entrance 16 of the respiratory system of patient 14 during exhalation interval 22 of immediate breathing cycle 24 when the first predetermined percentage of positive peak pressure value 38 is achieved. The next step includes continuing delivery of the gaseous fluid to entrance 16 of the respiratory system during subsequent inhalation interval 26 of successive breathing cycle 28. The final step is ending delivery of the gaseous fluid to the respiratory system during subsequent inhalation interval 26 of successive breathing cycle 28 when a second predetermined percentage of negative peak pressure value 36 is achieved. Furthermore, the step of commencing delivery of additional gaseous fluid to entrance 16 of the respiratory system of patient 14 during subsequent inhalation interval 26 of successive breathing cycle 28 when a third predetermined percentage of negative peak pressure value 36 is achieved can also be added after continuing delivery of the gaseous fluid to entrance 16 of the respiratory system during subsequent inhalation interval 26 of successive breathing cycle 28.

A second exemplary embodiment of an intermittent gas-insufflation apparatus employs a variable orifice valve such as a conventional tapered-needle valve. This second exemplary embodiment of the intermittent gas-insufflation apparatus employs the same general operational principles of the first exemplary embodiment of the intermittent gas-insufflation apparatus 10 except that a different type of valve is used in lieu of the first and second solenoid valves. Also, the second exemplary embodiment of the intermittent gas-insufflation apparatus requires some modification to the software program which controls controller 34. With modification to the software program, controller 34 is now operative to receive and process the sensor signals generated by sensor 32 during immediate breathing cycle 24 to calculate how much of a quantity of the gaseous fluid is required by the breathing efforts of patient 14. For the second exemplary embodiment of the present invention, it is preferred that sensor 32 detects a rate of change of the breathing pressure of the patient. Controller 34 is responsive to the sensor signals to actuate valve assembly 30 into the opened state so that the calculated quantity of gaseous fluid flows from source 12 of gaseous fluid to entrance 16 into the respiratory system of patient 14 during exhalation interval 22 of immediate breathing cycle 24 and into subsequent inhalation interval 26 of successive breathing cycle 28. Controller 34 is further responsive to actuate valve assembly 30 into the closed state during subsequent inhalation interval 26 of successive breathing cycle 28 when the calculated quantity of gaseous fluid is delivered to entrance 16 into the respiratory system of patient 14. It is preferred that valve assembly 30 actuates into the closed state before the negative peak pressure value of the subsequent inhalation interval of the successive breathing cycle is achieved.

The calculated quantity of the gaseous fluid to be delivered to the patient is predicated upon the immediate breathing cycle. So, as the patient's respiratory needs change, for example, as a result of increased physical activity, the calculated quantity of the gaseous fluid will also increase. Correspondingly, when the patient's physical activity decreases, changes in breathing pressure will be detected to cover the calculated quantity of gaseous fluid to also decrease.

The rate of change of pressure can be calculated by dividing a difference between two detected pressure values by a difference of respective times during which the pressure valves were detected. This is illustrated in FIG. 2 by angles 71. A skilled artisan would appreciate that this is a calculation of the "slope" of flow trace 70. Note that the rate of change of pressure can be calculated during the inhalation interval of the immediate breathing cycle during the exhalation interval of the immediate breathing cycle or even during the subsequent inhalation interval of the successive breathing cycle.

Additionally, controller 34 is further operative to determine a flow rate profile of the calculated quantity of the gaseous fluid for continuous flow thereof to entrance 16 into the respiratory system of the breathing patient during exhalation interval 22 of immediate breathing cycle 24 and subsequent inhalation interval 26 of successive breathing cycle 28. By way of example only and not of limitation, the flow rate profile is illustrated by the solid line flow trace 70 shown in FIG. 2. Since modification of the software program can determine the configuration of the flow rate profile as desired, the flow rate profile is selected from a group consisting of a constant flow rate profile as illustrated by flat solid line portion 68 of flow trace 70, a variable flow rate profile illustrated as the spiked solid line portion of flow trace 70 or a combination the fixed and the variable flow rate profile as illustrated in FIG. 2. Since the rate of change of pressure can be detected within the subsequent inhalation of the successive breathing cycle while the gaseous fluid is flowing to the entrance of the respiratory system of the patient, the flow rate profile of the flowing gaseous fluid can be instantly changed to facilitate complete and timely delivery of the calculated quantity of the gaseous fluid to the patient, if desired. This feature of the present invention has not heretofore been incorporated into any prior art. Obviously, the flow rate profile could be instantly modified, if desired, at any time during which the gaseous fluid is being delivered, i.e., during the exhalation interval of the immediate breathing cycle and the subsequently inhalation interval of the successive breathing cycle.

By way of example only, a maximum flow rate "MFR" of the calculated quantity of gaseous fluid flowing into entrance 16 of the respiratory system of the breathing patient during exhalation interval 22 of immediate breathing cycle 24 occurs shortly after beginning stage "BS" of inhalation interval 18 of the subsequent breathing cycle. Preferably, the flow rate profile of the gaseous fluid includes a flow rate range having a minimum flow rate of 0.5 liters per minute and a maximum flow rate of 0.5 liters per minute.

It follows from the second exemplary embodiment of the intermittent gas insufflation apparatus of the present invention, a method is employed for intermittently insufflating the gaseous fluid from the pressurized gaseous fluid source and into an entrance of a respiratory system of the breathing patient after the inhalation interval and during the exhalation interval of the immediate breathing cycle and into the subsequent inhalation interval of the successive breathing cycle. The first step is calculating the quantity of the gaseous fluid required to be delivered to entrance 16 of the respiratory system of patient 14 during one of inhalation interval 18 and exhalation interval 22 of immediate breathing cycle 24. The next step is commencing delivery of the calculated quantity of the gaseous fluid to entrance 16 of the respiratory system of patient 14 during exhalation interval 22 of immediate breathing cycle 24. The next step includes continuing delivery of the calculated quantity of the gaseous fluid to entrance 16 of the respiratory system of patient 14 into subsequent inhalation interval 26 of successive breathing cycle 28. The next step is ending delivery of the calculated quantity of the gaseous fluid to the respiratory system of patient 14 when delivery is complete during subsequent inhalation interval 26 of successive breathing cycle 28. It is preferred that a step of determining a desired flow rate profile for the delivery of the quantity of the gaseous fluid occurs simultaneously with the step of calculating the quantity of the gaseous fluid required to be delivered to entrance 16 of the respiratory system of patient 14 during one of inhalation interval 18 and exhalation interval 22 of immediate breathing cycle 24. It is also preferred that the step of delivering a maximum flow rate of the desired flow rate profile shortly after the beginning stage "BS" of subsequent inhalation interval 26 of successive breathing cycle 28. Of course, it is preferable to include a step of repeating the steps of this method for each series of consecutive immediate and successive breathing cycles.

A third exemplary embodiment of an intermittent gas insufflation apparatus of the present invention incorporates valve assembly 30 which includes a shape-memory alloy-film actuated valve (commonly referred to as a microflow valve). This third exemplary embodiment of the intermittent gas insufflation apparatus of the present invention employs the same operational principles of the embodiments described above except that minor modifications of the software program controlling controller 34 must be made. As with any conventional shape-memory alloy-film actuated valve, actuating this valve can be controlled whereby the opened state can be varied as dictated by the software program as the gaseous fluid flows from the source to the patient. Thus, flow rate of the gaseous fluid can be precisely controlled at any time during delivery of the gaseous fluid to the patient.

Given the three exemplary embodiments of the intermittent gas insufflation apparatus of the present invention described above, one of ordinary skill in the art would appreciate the advancement made in the art. Particularly, the intermittent gas insufflation apparatus of the present invention includes the controller coupled to and between the sensor and the valve assembly which is operative to receive and process the sensor signals generated during either the inhalation interval of the immediate breathing cycle, the exhalation interval of the immediate breathing cycle or the inhalation and exhalation intervals of the immediate breathing cycle. Although not by way of limitation, valve assembly actuates into the opened state at waning stage "WS" of the exhalation interval of the immediate breathing cycle and actuates into the closed state during later stage "LS" of the subsequent inhalation interval of the successive breathing cycle. Furthermore, the intermittent gas insufflation apparatus of the present invention employs a method for intermittently insufflating a gaseous fluid from a pressurized gaseous fluid source and into an entrance of a respiratory system of a breathing patient. The first step includes generating sensor signals during either of the inhalation interval of the immediate breathing cycle, the exhalation interval of the immediate breathing cycle or both the inhalation and exhalation intervals of the immediate breathing cycle. The next step includes processing the sensor signals during either the inhalation interval of the immediate breathing cycle, the exhalation interval of the immediate breathing cycle or both of the inhalation and exhalation intervals of the immediate breathing cycle to determine the quantity of the gaseous fluid to be delivered to the entrance of the respiratory system of the patient. The next step is then commencing delivery of the quantity of gaseous fluid to the entrance of the respiratory system of the patient during the exhalation interval of the immediate breathing cycle. The following step is continuing delivery of the quantity of the gaseous fluid to the entrance of the respiratory system of the patient into the subsequent inhalation interval of the successive breathing cycle. The next step is ending delivery of the quantity of the gaseous fluid to the respiratory system of the patient during the subsequent inhalation interval of the successive breathing cycle.

A skilled artisan would comprehend that the valve assembly can employ any type of valve, conventional or otherwise. Depending upon the needs of the patient, the valve assembly could employ a single solenoid valve, a single stepped solenoid valve, a single proportional valve or a single shape-memory alloy-film actuated valve. Also, for any of the exemplary embodiments described above, the present invention could incorporate an arrangement of solenoid valves, an arrangement of stepped solenoid valves, an arrangement of proportional valves, an arrangement of shape-memory alloy-film actuated valves and even an arrangement of any combination of these types of valves. Furthermore, the present invention could operate with the valve or valves normally in the opened state or normally in the closed state. Valves in the normally opened state would provide a "fail-safe" feature into the valve assembly whereby, for example, in the event of a power source failure, the valve or valves of the valve assembly would automatically actuate to the opened state. Thus, even without a power source, the patient would continue to receive oxygen at a default rate of flow, preferably at 2 liters per minute.

Additionally, the intermittent gas insufflation apparatus of the present invention could be used with a blood-oxygen concentration device to maintain an appropriate blood-oxygen concentration in a patient's blood stream. For example, with an oximeter operably connected to a patient's ear, the software program could again be modified so that the quantity of oxygen to be delivered to the patient is based upon feedback from the oximeter. Thus, a method is employed for maintaining at least a threshold amount of blood-oxygen concentration in the patient receiving supplemental oxygen from a supplemental oxygen delivery system. The first step includes monitoring the amount of blood-oxygen concentration in the patient. The next step is determining the amount of blood-oxygen concentration in the patient is below the threshold amount of blood-oxygen concentration. The next step is activating the supplemental oxygen delivery system until the amount of blood-oxygen concentration is at least the threshold amount of blood-oxygen concentration for the patient.

Operation

Referring again to FIG. 1, the insufflation gas, in this case oxygen, is supplied from source 12. The oxygen is transmitted via gas supply tubing 40 to respective ones of first and second solenoid valves V1 and V2. Via lines 44 and 46, the gas communicates from first and second solenoid valves V1 and V2 with manifold 48. From manifold 48, gas is transmitted via gas delivery tube 52 to the nasal cannulae 50. At least one sense tube 53 is also connected to the cannulae 50, preferably isolated from communication with oxygen passing to the patient gas delivery tube 52. The sensing tube 53 is connected to sensor 32 which is a pressure transducer 32 supplied by SenSym Inc. of Palo Alto, Calif. The pressure transducer 32 is powered by power source 35 which uses power line 78 to supply either 110 VAC converted to 5 VDC by AC/DC converter 80 or, alternatively, direct current from a battery 82 which is connected electrically in line with a battery low sensor 84 whose function will be more fully described hereinafter. Additional power outputs from the power source 35 are provided and designated PS. The PS power supply output is shown in FIG. 1 to communicate electrical power via lines 58 and 60 to first solenoid valve V1 and second solenoid valve V2. Power source 35 also provides electrical power to the microprocessor 34 via line 79. The output line 86 of the pressure transducer is also connected to an input in the microprocessor 34, which is also labelled U1 in FIG. 4.

In operation, the sensing tube 53 will be under positive pressure during a patient's exhalation and negative pressure during a patient's inhalation when the nasal cannulae 50 is fitted to a normally breathing patient. Referring to FIG. 2, the top horizontal sinusoidal line represents a trace of a patient's breathing cycle where the curve above the straight horizontal line indicates the positive pressure in the sensing tube 53 (base line 20) (FIG. 1) during exhalation and the curve below the line represents the negative pressure in the sensing tube 53 during inhalation. The pressure differences over the period of a patient's breathing cycle are sensed by the pressure transducer which directly communicates with the pressure of the gas in the sensing tube 53. Typically, the pressure transducer will provide a proportional analog signal having positive and negative voltage values representative of the positive and negative pressure variants of a patient's exhalation and inhalation as shown by the graph on FIG. 2. This signal is fed via output line 86 to the microprocessor 34 or U1.

In the microprocessor 34 or U1, the positive and negative voltage containing signal stream or waveform is converted into a digital format and is continuously stored in the random access memory of the microprocessor U1. The stored digital signal is accessed continuously during the operation of the device for determination of the occurrence of various preselected conditions which actuate or trigger the operation of first and second solenoid valves V1 and V2. During the exhalation interval (see FIG. 2) of the immediate breathing cycle, the maximum positive pressure is indicated at positive peak pressure value 38. When the software in the microprocessor U1 verifies that a maximum value reached, a predetermined fraction of that signal value is created by the microprocessor and the digitized, stored waveform signal is interrogated and compared with that created value. When that value is reached, an enable signal is produced in the microprocessor to activate valve driver 62 which in turn actuates first solenoid valve V1 opening it to the source 12 of oxygen via tubing 40 and the nasal cannulae 50 via valve tubing 44 and 46 of respective ones of first and second solenoid valves V1 and V2 and gas delivery tube 52. The rate of flow of the oxygen is regulated by the size of an orifice (not shown) inherent in the valve and is typically about 2 liters per minute for first solenoid valve V1.

Another preselected fraction of the maximum negative inhalation pressure is sensed. This value can be set by the respiratory therapist or patient to accommodate changes in physical activity and the set points will have been predetermined for each patient by monitoring blood gases during selected activities. Within the limits of adjustability of an amount of oxygen to be delivered, there can be incorporated in such a fixed flow device a degree of patient need accommodation not hitherto obtained.

Likewise, second solenoid valve V2 can be replaced with a variable orifice (not shown) or variable flow valve (not shown) which can be programmed to deliver the predetermined amount of oxygen insufflation gas during the inhalation interval before the predicted maximum negative pressure so as to take full advantage of the benefits and advantages of the present invention.

This oxygen continues to flow to the patient until the point in the breathing cycle when trigger point "LS" is reached. The trigger point is generated by the microprocessor U1 when the value of the pressure transducer output reaches a preselected fractional value of the peak value of the inhalation interval of the immediate breathing cycle, which was determined and stored by the microprocessor at the peak of the inhalation interval during the immediate breathing cycle. Contemporaneously, the second enable signal is routed to valve driver 62 which is energized/actuated causing oxygen to flow from gas supply tubing 40 and through valve tubing 46 from whence it exits through the gas delivery tube 52 to the patient. The rate of flow of oxygen is determined by the size of an orifice restrictor at the valve seat (not shown) of second solenoid valve V2. This oxygen flow continues until 33% of the peak negative pressure value of the inhalation interval of the immediate breathing cycle is reached in the subsequent inhalation interval. Simultaneously, the microprocessor, U1, will be measuring the present inhalation interval to calculate and store the trigger point value, i.e., 33% of the negative peak pressure value of the immediate inhalation interval, for the generation of the next trigger point which is required in the succeeding breathing cycle.

The sequence described hereinbefore for the embodiments is repeated for each breathing cycle. If the patient's need for oxygen increases, e.g., from exertion or exercise, the appropriately programmed present invention automatically accommodates the increased need by delivering a predetermined amount of oxygen for each exhalation/ inhalation interval of each breathing cycle. Operation of the present invention is further facilitated by the following switches, lights and an alarm. These are Shown in FIG. 1:

(a) "TEST" Switch, TS-1, is a multi position digital switch which can be used by the operator to run a series of functional tests on the device to check its operation prior to placing the device into use with a patient. These tests can also be used as a diagnostic tool in the event of equipment malfunction.

(b) "LO BPM" is the label placed on light L-1, designating "Low Breaths Per Minute". This light is illuminated by a signal from the microprocessor, U1, when the patient's breathing rate decreases to an unsafe level.

(c) "ALARM", A-1, is sounded by a signal from the microprocessor, U1, whenever the breathing rate is too low as determined in (b) above, or when the battery voltage decreases below a preset level which would provide for correct operation of the device. The present invention might include a switch so that when the alarm sounds, the patient could manually switch to the default rate of flow.

(d) "VALVE ON", light L-2, is a green light connected across either one or both of the solenoid valves, so that the light is illuminated whenever the valves or valve is activated thereby signalling the cycling of the valve(s) with each breath.

(e) "LO BAT", L-3, is the low battery light. This red light is illuminated by a signal from the microprocessor, U1, at the same time that the ALARM is sounded. Additionally, this provides the information that the alarm is sounded. Additionally, this provides the information that the alarm was sounded because the battery voltage was low and not that the patient was having breathing difficulty. Again, the patient may employ the switch for the default rate of flow when the low battery light illuminates.

DETAILED DESCRIPTION OF CIRCUITS

Power Source

Figure 3:
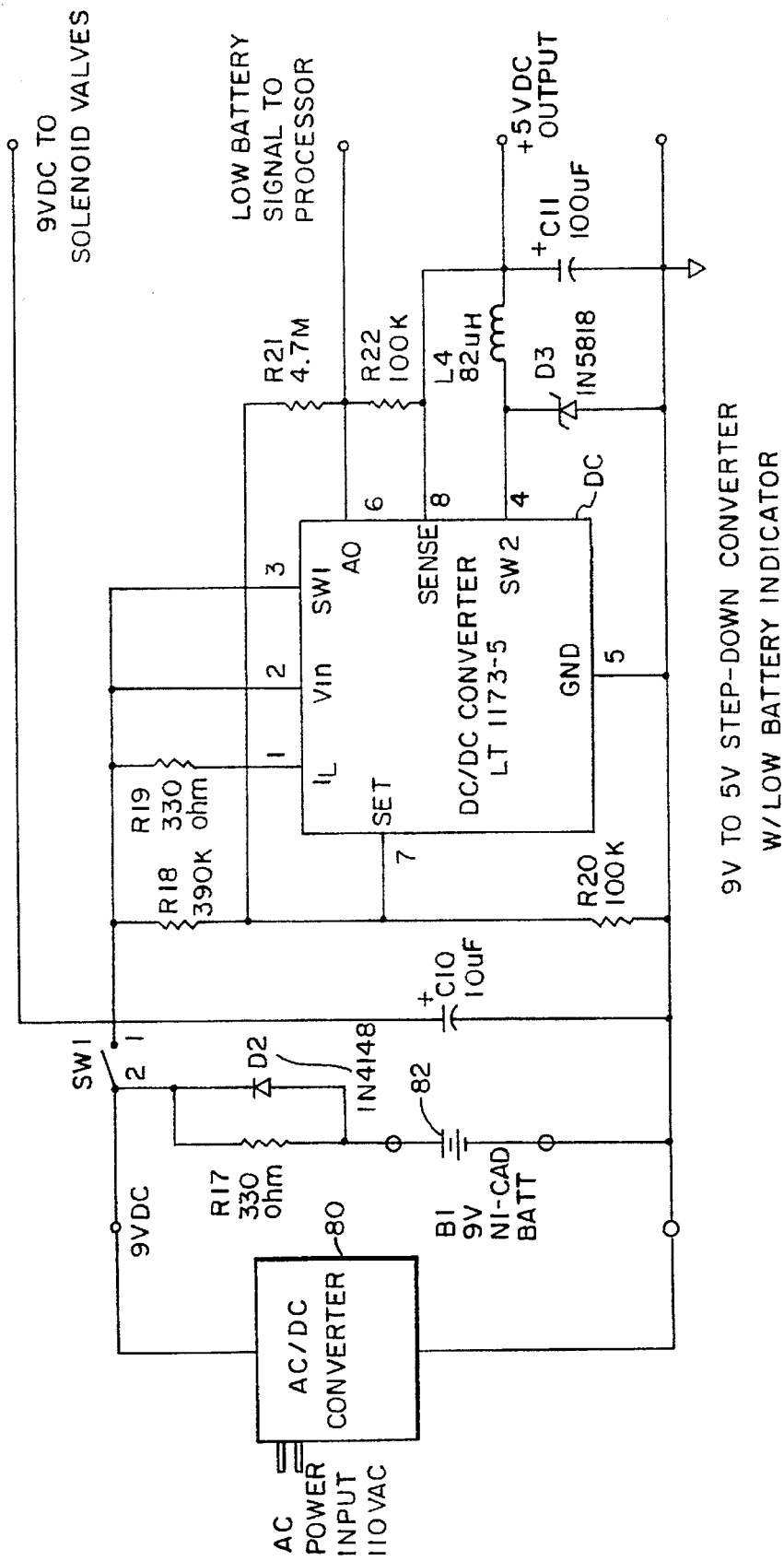
FIG. 3 is a schematic diagram of a power source accompanied by an electrical schematic diagram which is incorporated into the intermittent gas-insufflation apparatus of the present invention.

With reference to FIG. 3, the present invention is normally powered using 110 VAC which is converted to 9 VDC via the AC/DC converter 80. The 9VDC trickle charges the battery, 82 or B1, through the charging resistor, R17. The value of R17 is selected to prevent damage to the battery. When the AC/DC converter is unplugged from the system, the battery B1 provides backup power to the system. The diode D2 bypasses the charging resistor R17 to enable adequate system power in the backup mode. Capacitor C10 stores sufficient charge to supplement any large power demands when the solenoid valves are activated. The 9 VDC is applied to the step-down DC-DC converter circuit DC which provides +5VDC regulated power to the electronic circuits when switch SW1 is in the ON position. The 9 VDC is also applied to the solenoid valves, V1 and V2. Converter DC is configured as a step-down converter. The resistor R19 is selected to limit the maximum output current at +5 VDC. The filter circuit comprised of diode D3, inductor L4, and capacitor C11, smooths the output ripple to an acceptable level. Regulation is provided by feeding back the output signal to the SENSE input, pin 8, of the DC-DC converter. A low battery signal is generated in the DC-DC converter. The trip point is determined by the value of resistor R18, and the network of resistors R20, R21 and R22. The low battery signal, AO, provided at pin 6 of the DC-DC converter and sent to the microprocessor input pin 34, as shown in FIG. 4.

Valve Driver/Power Saver

Figure 4A:
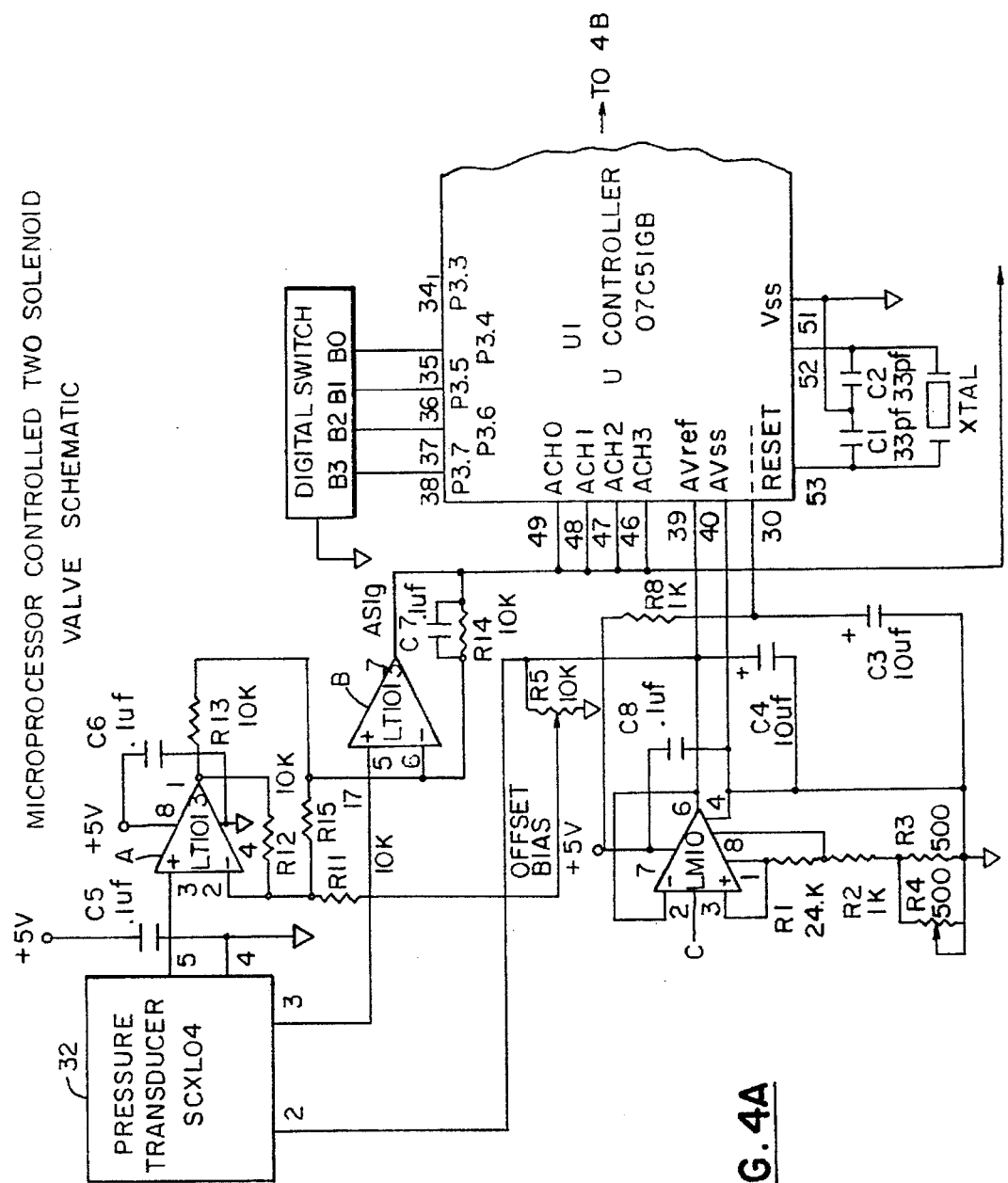
FIG. 4 is a schematic diagram of a sensor, a reference voltage generator, a controller in a form of a microprocessor and a valve assembly including a first solenoid valve and a second solenoid valve which are incorporated into the intermittent gas-insufflation apparatus of the present invention.

In FIG. 4, the microprocessor, U1, provides turn-on signals to actuate solenoid valves V1 and V2. The valves will remain actuated as long as the turn-on signal is present. The drive circuitry for the solenoid valve V1 consists of a MOS-FET semiconductor Q1 to actuate solenoid valve V1, and a MOS-FET Q3 with a resistor R15', to hold the valve in the actuated position at reduced power. The power saving feature operates by switching the turn-on signal from Q1 to Q3 immediately after the solenoid valve is actuated. The current required to hold the solenoid valve actuated is less than the current required for actuation and is set by selecting the value of R15. The diode D1 clamps the voltage across the solenoid valve to prevent arcing and overshoot. Similarly, the drive circuitry for the solenoid valve V2 consists of MOS-FETs Q2, Q4 and resistor R16. A light emitting diode L2, and its current limiting resistor R6, are placed across solenoid valve V2, to indicate that the valve has been actuated. Each turn-on signal will result in the illumination of the light emitting diode for the duration of the signal.

Alarm

In FIGS. 1 and 4, the alarm is a piezoelectric device that emits an audible sound when activated by the microprocessor. The combinations of conditions to cause an alarm are programmed into the microprocessor. The alarm is sounded when any of the predetermined conditions are sensed.

Diagnostic Outputs

Signals are available to aid in data logging and troubleshooting. These signals can be accessed and displayed with the use of auxiliary equipment such as an oscilloscope, a chart recorder, etc.

Digital Switch

In FIGS. 1 and 4, the digital switch TS-1 is a multi-position rotary switch that provides a four digit binary coded decimal (BCD) output. The output of the BCD switch is connected to the microprocessor at pins 35, 36, 37 and 38. The selected codes will address preprogrammed diagnostic routines that will perform calibration, system setup and diagnostic operations.

Reference Voltage Generator

In FIG. 4, the reference voltage generator circuit consists of a reference voltage and operational amplifier C. Resistor R1 provides the feedback for the amplifier C. Resistors R2, R3 and POT R4 provide input resistance. POT R4 provides adjustability of the reference voltage output.

The precision reference voltage is utilized by the microcontroller analog to digital converter for its reference voltage. Also, the reference voltage provides a precision and stable voltage to the pressure transducer bridge circuit.

The offset bias voltage utilized by the pressure transducer circuit is provided at the center tap of POT R5. The voltage is adjustable between 0 volts and the reference voltage.

Pressure Transducer Circuit

Also in FIG. 4, the pressure transducer circuit consists of a standard differential pressure transducer 32 and differential amplifiers A and B. The pressure transducer is a typical variable resistance bridge circuit. The outputs of transducer 32 are connected to operational amplifiers A and B via output pins 5 and 3, respectively. Pin 2 is the reference voltage line and pin 4 is the return input (ground).

The operational amplifiers A and B are each configured as a differential amplifier with high gain. The offset bias voltage provides an offset output voltage at pin 7 of B also defined as Asig. The output Asig is adjusted for ½ the reference voltage at ambient pressure. The offset voltage provides a means to output a positive and negative pressure measurement.

Microcontroller

The microprocessor U1 or 34, also known as microcontroller, is a standard Intel Part MC80C51GB. The basic features are the following:

8 bit computer architecture 256 random access memory 4K programmable memory 8 channels of analog to digital conversion The crystal (XTAL) attached at pins 52 and 53 provides the control of the operating frequency for the microcontroller. The reference voltage generator provides a power on reset signal ($\overline{RESET}$) to the microprocessor. The signal is set to a low voltage upon initial power turn-on. The microprocessor is held inactive until the signal goes to a logic high level. At this time, the microprocessor starts executing stored programmed instructions. The process flow is discussed hereinafter. The input signals to the microprocessor are the analog pressure transducer signal Asig and digital signal Battery Lo (pin 34-P3.3). The Asig are inputted to the first four analog channels for digital conversion ACH0-pin 49, ACH1-pin 48, ACH2-pin 47, ACH3-pin 46.

Outputs from the microprocessor are the following digital signals. P1.0-pin 22 and P1.1-pin 23. P1.0 commands the valve driver circuit V2 and P1.1 commands the valve driver circuit V1.

Output at P1.7-pin 29 is connected to an audible alarm buzzer. The microprocessor generates various audible frequencies to denote different alarm indications. The output P1.6-pin 28, P1.5-pin 27 drive light emitting diodes (LED) to indicate low breathing rate and Battery Lo voltage, respectively.

Program Flow

Figure 5A:
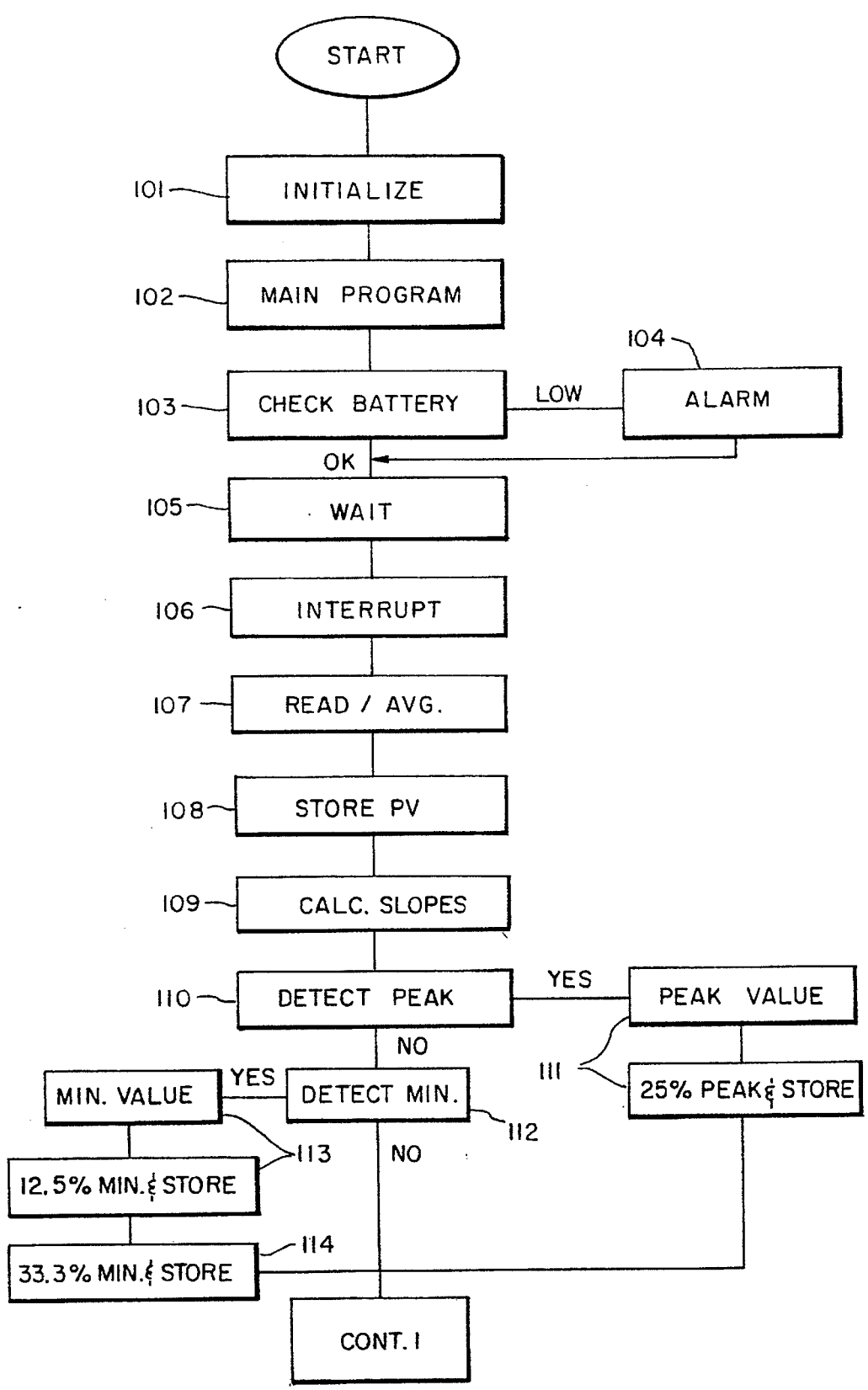

The following describes the process flow that will be coded into the microcontroller. FIG. 5 shows the flow of the process that monitors the exhalation and inhalation pressures in real-time and process this information to determine the start and stop of the turn on of the $O_2$ valves.

Upon completion of the power-on reset, the stored program initializes the microprocessor. The initialization (101) consists of setting up the 10 ms interrupts timer, baud rate timer, serial port, A/D converter and input/output ports of the microprocessor. Once initialization has been completed, the program enters the main program (102). The main program starts with a check of the Battery Lo signal P3.3 (103). If the battery voltage level low is detected, the processor goes to the alarm routine (104). The processor turns on the Lo Battery LED indicator and also starts a low frequency beep on the audible alarm. Once completed, the program continues and goes into a wait mode (105).

Upon receipt of a 10 ms interrupt, the program services the interrupt routine (106). This involves starting the analog-to-digital conversion and reset in the interrupt timer. The next step is to read the four analog converted voltages (107) after a fixed time delay from the start of A/D conversion. This is to make sure conversion is complete. The four valves are averaged and labeled present value. The present value is stored into the last byte of the last in-first out (LIFO) memory of 16 bytes (108). Slopes are calculated (109) either as values or as indicators (positive or negative). Slopes are calculated between first and last, last and third to last, last and fifth to last, and third to last, and fifth to last. The flow continues by monitoring present value with the last highest value (110). If the present value is greater than the last highest value, the peak value is updated with the present value. If the present value is less than the peak value, the peak value is unchanged. To determine if a peak has been detected, the following conditions must be present:

1) the long slope must be negative (slope first to last)

2) the short slope must be negative (slope fifth to last and last)

3) in exhalation interval of the cycle.

If peak detection is enabled, the next step is to retrieve the peak value (111) and divide by 4 to get 25% of the peak value. This then becomes the start value for purge on.

The detection of the minimum value (112) is very similar to the peak detection process with the following differences. Minimum detection criteria is the following:

1) the long-slope must be positive 2) the short-slope must be positive 3) in inhalation interval of the cycle.

When minimum detection has been detected, the minimum value is retrieved (113, 114) and 12.5% and 33% values are calculated and stored. These values are used for start of the main $O_2$ burst and turn-off of the $O_2$, respectively, on the next inhalation cycle. During the cycle in which the peak detection occurs, the 25% value of the peak is stored and compared with the present pressure value (115). If the present value is less than or equal to the 25% value of peak, the microprocessor commands the valve driver V1 on (116). The V1 valve opens and provides a 2 L/M flow to purge the $O_2$ line.

During the same cycle and during the inhalation period, the processor compares the present pressure value with the 12.5% minimum value of the previous cycle (117). When the present pressure value equals or is less than the 12.5 minimum value, the microprocessor turns on the high flow valve V2 (118).

The valves are turned off when the present pressure value is greater or equal to 33⅓% of the minimum value of the previous cycle (119, 120). The end of the main program flow (121) shifts the LIFO memory by one byte for set up of the next 10 ms measurement.

Also, the watch dog timer is reset. The watch dog timer reinitializes the microprocessor if, for some reason, the program does not reset the watch dog timer.

The flow continues by monitoring the inhalation cycles. When no inhalation is detected, the microprocessor will turn on the audible alarm and LED indicator. Also, the Lo flow valve V1 will be enabled to provide continuous Lo $O_2$ flow.

The program flow continues with the process by returning to the start of main program and waiting for the 10 ms interrupt.

The intermittent gas-insufflation apparatus of the present invention provides significant advancements and benefits over the prior art. The intermittent gas-insufflation apparatus of the present invention determines the appropriate quantity of oxygen to be delivered to the patient during an immediate breathing cycle and adjusts appropriately to supply the quantity of oxygen commensurate with the physical activity of the patient.

The intermittent gas-insufflation apparatus delivers the appropriate quantity of oxygen continuously during an exhalation interval of the immediate breathing cycle and into an inhalation interval of a subsequent breathing cycle. This results in purging some of the air remaining in the nasal passage from the prior breath and enriches a remaining portion thereof. Further, a high-rate pulse of oxygen is delivered at approximately the beginning of the subsequent inhalation interval of the successive breathing cycle which is optimum. The intermittent gas-insufflation apparatus can determine an appropriate flow rate profile for delivering the oxygen during the exhalation interval of the immediate breathing cycle and the inhalation interval of the successive breathing cycle and, if desired, can modify the flow rate profile even while oxygen is being delivered to the patient. The intermittent gas-insufflation apparatus can terminate delivery of oxygen during the subsequent inhalation interval of the successive breathing cycle and, preferably before the negative peak pressure value generated in the immediate breathing cycle is reached in the successive breathing cycle. This feature saves wastage of costly oxygen, particularly since oxygen is delivered when it could be best utilized by the patient.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

What is claimed is:

1. A method for maintaining a preselected blood-oxygen concentration in a patient receiving supplemental oxygen from an intermittent supplemental oxygen delivery system comprising the steps of:

a) monitoring the blood-oxygen concentration in a patient to determine whether the blood-oxygen concentration of the patient is below the preselected blood-oxygen concentration;

b) providing an intermittent supplemental oxygen delivery system having means for delivering oxygen to only one entrance to a patient's respiratory system and responsive to a patient's breathing cycle sensed by monitoring the pressure differences at the other entrance to the patient's respiratory system to intermittently provide oxygen delivery only in the latter portion of the patient's expiratory cycle and the initial portion of a patient's inspiratory cycle at preselected flow rates and time duration; and c) supplying a larger volume of oxygen to a patient during the latter portion of the expiratory phase of a patient's breathing cycle from the intermittent oxygen delivery system when a patient's blood-oxygen concentration is below the preselected blood-oxygen concentration.

2. A method according to claim 1 wherein the provided means for delivering oxygen consists essentially of intermittent gas-insufflation apparatus having:

(a) a valve assembly adapted to be disposed between and in fluid communication with a source of oxygen gas and a first entrance into the respiratory system of a patient and operative to actuate between a closed state whereby fluid communication is interrupted so that the oxygen gas is prevented from flowing from the source of oxygen gas to said first entrance into the respiratory system of the patient and an adjustable opened state whereby fluid communication is established so that the oxygen gas flows at preselected rates from the source of oxygen gas to said first entrance into the respiratory system of a patient;

(b) a sensor in fluid communication with a second entrance into the respiratory system of the breathing patient and operative to detect changes in breathing pressure of a patient relative to an ambient pressure environment throughout the exhalation and inhalation intervals of an immediate breathing cycle of a patient and to generate sensor signals characteristic of the changes in the breathing pressure of the immediate breathing cycle; and (c) a controller coupled to and between said sensor and said valve assembly and operative to receive and process the sensor signals to determine a positive peak pressure value which occurs during the exhalation interval of the immediate breathing cycle, and a negative peak pressure value which occurs during the inhalation interval of the immediate breathing cycle, said controller responsive within the exhalation interval of the immediate breathing cycle to actuate said valve assembly into the opened state so that the oxygen gas flows from the source of oxygen gas to said first entrance into the respiratory system of the patient during at least the latter portion of exhalation interval of the immediate breathing cycle after the positive peak pressure value is achieved, said controller further responsive within the subsequent inhalation interval when a second predetermined percentage of the negative peak pressure value is achieved to actuate said valve assembly into the closed state so that the oxygen gas is prevented from flowing from the source of oxygen gas to said first entrance into the respiratory system of the patient before the subsequent inhalation interval of the breathing cycle terminates, said controller being capable of implementing the flow of a variable volume of oxygen during the latter portion of a patient's exhalation cycle in response to variations in the monitored blood-oxygen concentration of a patient.

3. A method according to claim 1 wherein the provided means for delivering oxygen includes an intermittent gas-insufflation apparatus having:

(a) a valve assembly adapted to be disposed between and in fluid communication with a source of oxygen gas and only a first entrance into the respiratory system of patient and operative to actuate between a closed state whereby fluid communication is interrupted so that the oxygen gas is prevented from flowing from the source of oxygen gas to said first entrance into the respiratory system of the patient and an opened state whereby fluid communication is established so that the oxygen gas flows from the source of oxygen gas to said first entrance into the respiratory system of the patient;

(b) a sensor in fluid communication with only a second entrance into the respiratory system of the breathing patient and operative to detect changes in breathing pressure of the patient relative to an ambient pressure environment throughout exhalation and inhalation intervals of an immediate breathing cycle of the patient and to generate sensor signals characteristic of the changes in the breathing pressure of the immediate breathing cycle; and (c) a controller coupled to and between said sensor and said valve assembly and operative to receive and process the sensor signals generated by said sensor during the immediate breathing cycle which measured peak expiratory and inspiratory pressures and to calculate the volume of oxygen to be intermittently delivered to a breathing patient during at least the expiratory interval of a successive breathing cycle, said controller further operative in response to the sensor signals to actuate said valve assembly into the opened state so that the calculated quantity of oxygen gas begins to flow from the source of oxygen gas to only said first entrance into the respiratory system of the patient during the exhalation interval of the successive breathing cycle.

* * * * *